(12) United States Patent
Fontana

(10) Patent No.: US 9,095,690 B2
(45) Date of Patent: *Aug. 4, 2015

(54) CANNULA FOR DISPENSING FLUID PRODUCTS, PARTICULARLY FOR VAGINAL AND RECTAL APPLICATIONS

(75) Inventor: Antonio Fontana, Carpi (IT)

(73) Assignee: LAMEPLAST S.P.A., Frazione Rovereto Sul Secchia (IT)

( * ) Notice: Subject to any disclaimer, the term of this patent is extended or adjusted under 35 U.S.C. 154(b) by 402 days.

This patent is subject to a terminal disclaimer.

(21) Appl. No.: 13/145,126

(22) PCT Filed: Feb. 4, 2010

(86) PCT No.: PCT/IB2010/000215
§ 371 (c)(1),
(2), (4) Date: Jul. 19, 2011

(87) PCT Pub. No.: WO2010/089651
PCT Pub. Date: Aug. 12, 2010

(65) Prior Publication Data
US 2011/0282304 A1    Nov. 17, 2011

(30) Foreign Application Priority Data
Feb. 9, 2009  (IT) .............................. MO2009A0029

(51) Int. Cl.
*A61M 31/00* (2006.01)
*A61F 5/451* (2006.01)
*A61M 5/315* (2006.01)

(52) U.S. Cl.
CPC ................. *A61M 31/00* (2013.01); *A61F 5/451* (2013.01); *A61M 5/31515* (2013.01); *A61M 2210/1475* (2013.01)

(58) Field of Classification Search
CPC ................... A61M 31/007; A61M 2210/1067; A61M 2210/1475; A61M 2005/31518; A61M 5/31515; A61M 31/00; A61F 5/451
USPC ............ 604/16, 111, 200, 256, 181; 206/364, 206/365
See application file for complete search history.

(56) References Cited

U.S. PATENT DOCUMENTS

2006/0264802 A1   11/2006   Fontana
2008/0086098 A1   4/2008    Fontana

FOREIGN PATENT DOCUMENTS

EP   0099457   *   5/1983
EP   1 518 574       3/2005

(Continued)

OTHER PUBLICATIONS

International Search Report issued on Aug. 10, 2010 in International Application No. PCT/IB2010/00215.

*Primary Examiner* — Aarti B Berdichevsky
*Assistant Examiner* — Laura Schell
(74) *Attorney, Agent, or Firm* — Stein IP LLC

(57) ABSTRACT

A cannula (1) for dispensing fluid products, particularly for vaginal and rectal applications, comprises:
a tubular body (2) for containing a fluid product (P), having a first extremity (2a), at which a dispenser opening (3) is formed, and a second open extremity (2b), opposed to the first extremity (2a).
A cover cap (4) is fitted onto the tubular body (2) to close the dispenser opening (3).
A closing body (5) associated with the tubular body (2) closes the second extremity (2b). The closing body comprises a first element (6) and a second element (7) made in a single body piece and joined along tearable connection means (8, 9, 10). The second element (7) removable by tearing off the first element (6) to act as a anti-tampering seal. The first element (6) is a cylinder partially insertable through the second extremity (2b) to function as a sliding piston inside the tubular body (2) once the second element (7) has been torn off. The cover cap is converted to a push rod for moving the piston by removing longitudinal sections of the cover cap, and then folding over the remaining sections to reduce the cross-section of the push rod.

4 Claims, 4 Drawing Sheets

(56) References Cited

FOREIGN PATENT DOCUMENTS

| WO | WO 2004/014476 | * | 2/2004 | | |
|----|----------------|---|--------|---|---|
| WO | WO 2004/014476 A1 | * | 2/2004 | ............ | A61M 31/00 |
| WO | WO 2006/134464 | | 12/2006 | | |

* cited by examiner

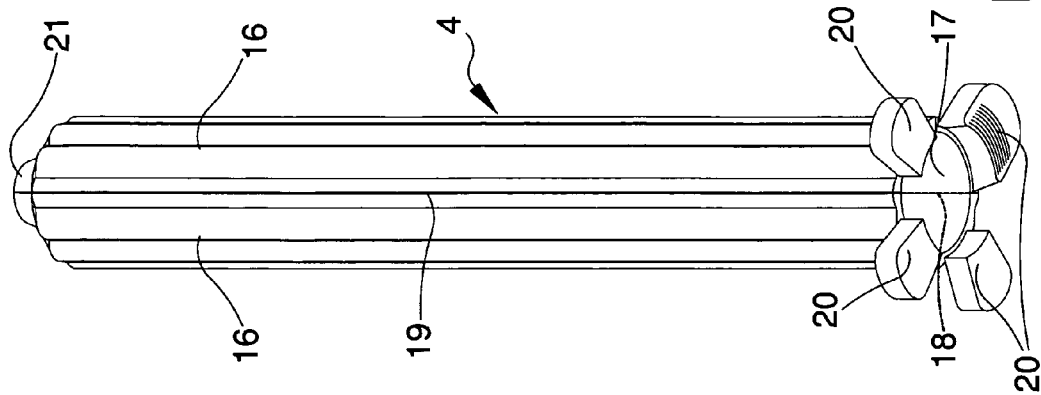
Fig. 5
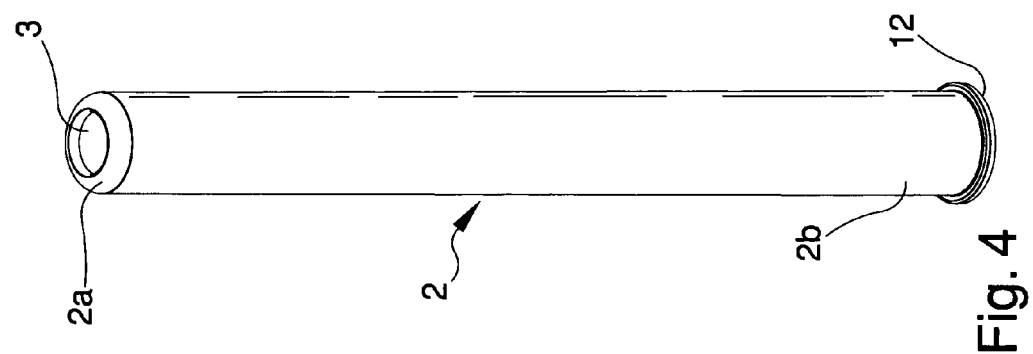
Fig. 4
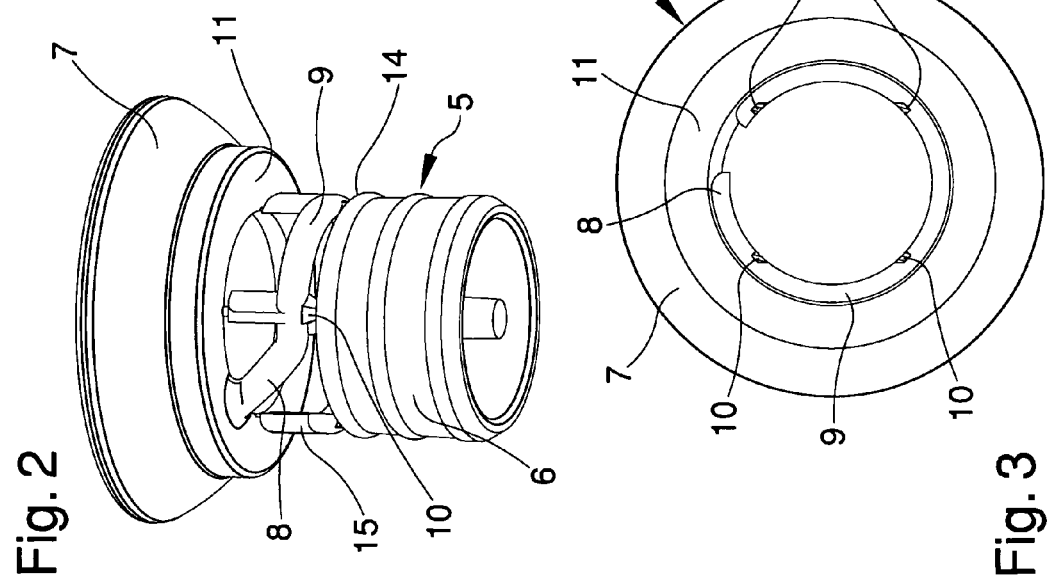
Fig. 2
Fig. 3

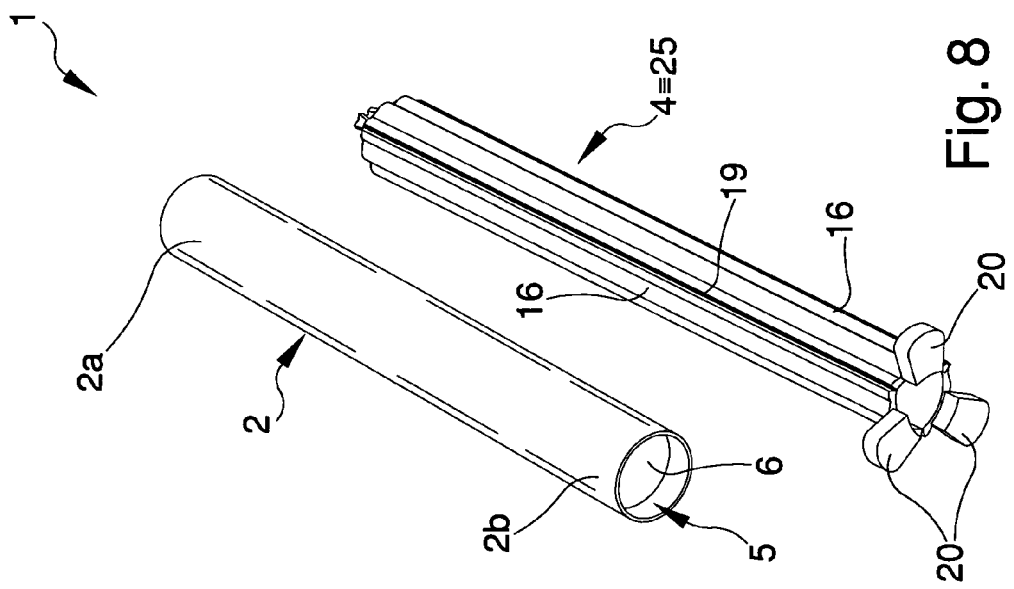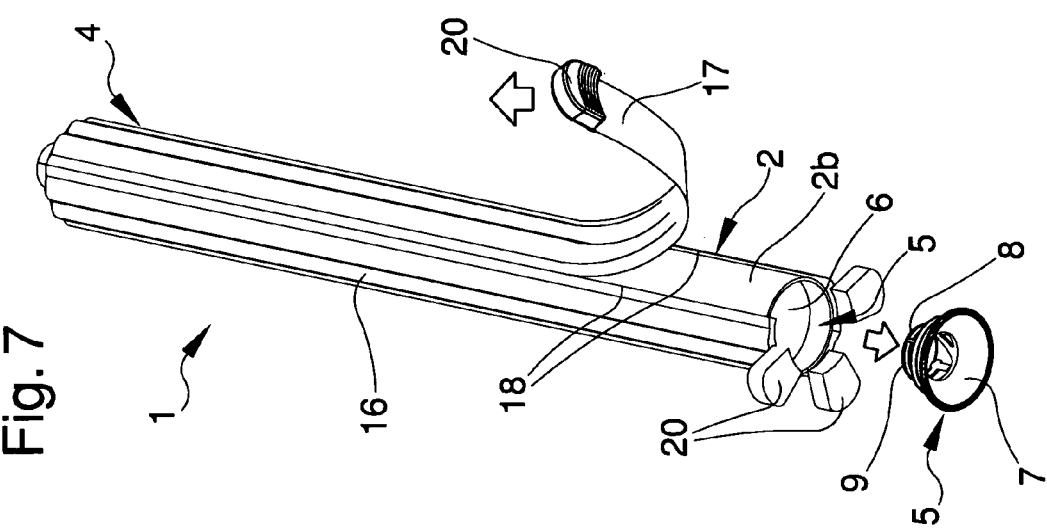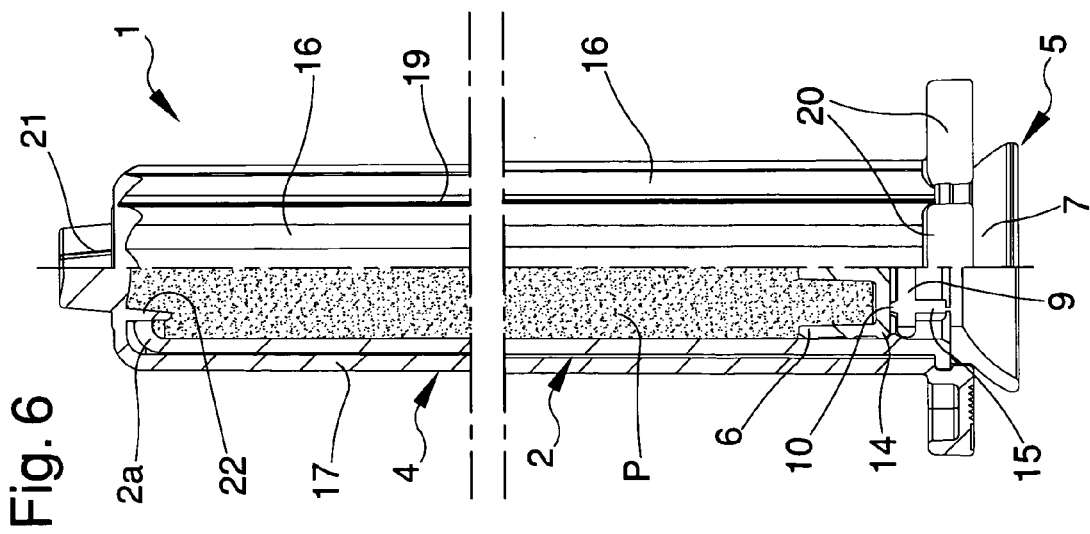

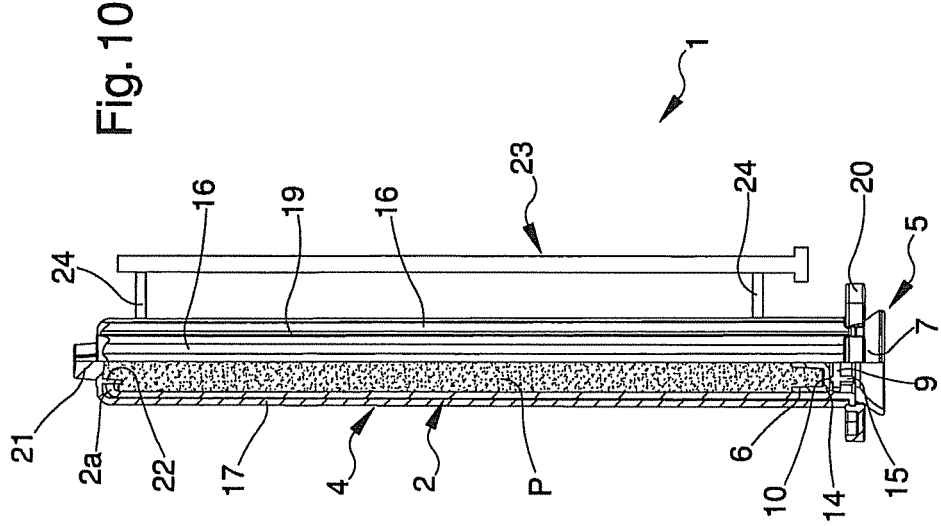
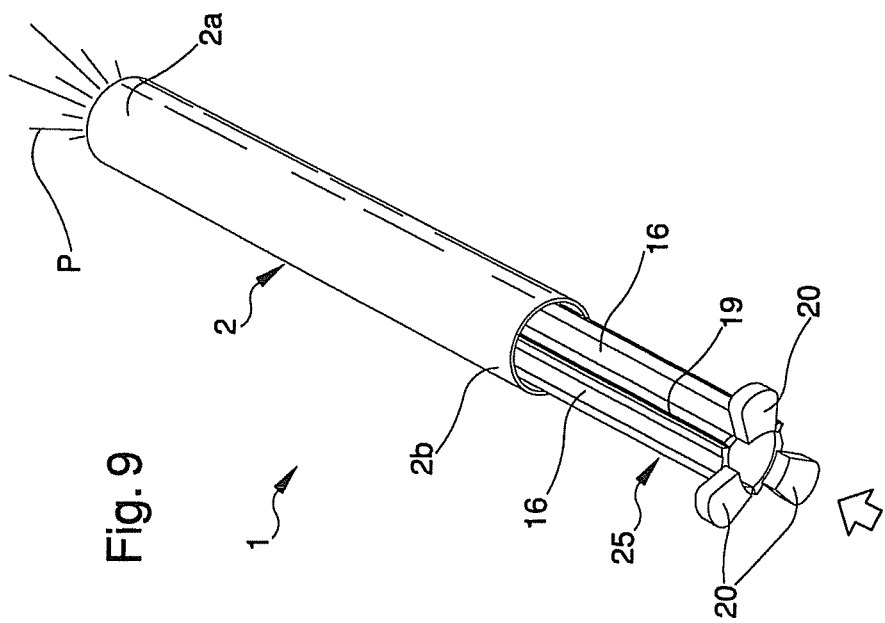

CANNULA FOR DISPENSING FLUID PRODUCTS, PARTICULARLY FOR VAGINAL AND RECTAL APPLICATIONS

CROSS-REFERENCE TO RELATED APPLICATIONS

This application claims the benefit of PCT International Patent Application No. PCT/IB2010/000215, filed Feb. 4, 2010, and Italian Patent Application No. MO2009A000029, filed Feb. 9, 2009, in the Italian Intellectual Property Office, the disclosures of which are incorporated herein by reference.

BACKGROUND OF THE INVENTION

1. Field of the Invention

The present invention relates to a cannula for dispensing fluid products, particularly for vaginal and rectal applications.

2. Description of the Related Art

Cannulas are known for dispensing medical fluid products which are used, in particular, for vaginal and rectal applications and which are generally sold in packs together with tubes or bottles containing the fluid products.

The known cannulas are composed of a cylinder suitable for containing the product and a piston integral with the extremity of a push rod, the piston sliding within the interior of the cylinder.

The cylinder has an open extremity that can be coupled with the dispenser mouth of the tube, to introduce into the cylinder itself the quantity of product to be applied, and through which the introduced product is dispensed.

The opposite extremity of the cylinder is closed by a bottom which has a hole, into which a push rod is inserted in a sliding manner, and which acts as a piston stop element to prevent its withdrawal.

The dispensing of the product introduced into the cannula occurs by moving the push rod to slide the piston towards the open extremity of the cylinder.

These known cannulas have a number of drawbacks among which must be recalled that they are rather complex in terms of structure and that, being for hygienic reasons of the single-use type and requiring a push rod for each cylinder, they produce a considerable waste of materials.

To overcome such drawbacks, cannulas are known composed of one cylinder, which has the opposite extremities open, and inside of which a piston is fitted in sliding fashion with a push rod separated from the piston and removably coupled to it.

At the opposite extremities of the cylinder, undercuts or stop shoulders are located for stopping the sliding of the piston and preventing this from coming out as a result of the action of the push rod.

These latter cannulas can be sold in packs containing a single push rod, a plurality of empty single-use cylinders to be used for the different applications, and one or more product tubes.

In this case one of the two extremities of the cylinders can be coupled with the dispenser mouth of the tube for the introduction of a product into the cylinders themselves, while the opposite extremity acts as a passage for the push rod.

These latter known cannulas have made it possible to curb the consumption of materials; the same push rod, in fact, can be used with a plurality of cylinders.

Nevertheless, these cannulas are not without drawbacks as well, tied above all to the need to use of one or more tubes of product to load the cylinders before use.

To overcome this drawback, an alternative type of so-called "pre-filled" cannula is known, meaning that the cannula is purchased with the cylinder already filled with the product to be applied, and with closing caps at the two opposite extremities which are removed at the time of use.

The pre-filled cannulas are not without drawbacks however, including the fact that they are of rather complex construction and that they have rather high production costs and times.

The cylinders, the pistons, the push rods and the closing caps in fact are normally made by molding polymer materials, in several pieces (at least five), separated from one another and subsequently assembled. This assembly involves the design and building of various molds and laborious assembly operations which negatively affect the production costs and times of the cannulas, as well as producing considerable and costly material waste.

From the patent WO 2004/014476 on the other, hand a particular type of pre-filled cannula is known in which the cylinder and the piston are made in a single body piece and, at an extremity of the cylinder, are joined together along a connection line with tearable weakened section.

The opposite extremity of the cylinder is closed by means of a tear-off film.

This particular type of pre-filled cannula also has a number of drawbacks. For example the fabrication of the piston in a single body piece with the cylinder is considerably complicated and hard to achieve in practice.

It should also be considered that big difficulties of a practical-manufacturing nature are also attributable to the use of the tear-off film.

Another type of pre-filled cannula is on the other hand known from EP 1 518 574 and comprises a push rod that can be extended by means of a telescopic rod system between a retracted configuration and an elongated configuration.

The push rod is made in retracted configuration together with the cylinder at an extremity of same.

The opposite extremity of the cylinder is instead closed by a cover cap made to fit over the cylinder permanently along its entire length until it joins at the base of the push rod.

The cannula described in EP 1 518 574 is also afflicted by various drawbacks, for the push rod involves the manufacture and the assembly of a plurality of telescopic elements, with consequent increase in times and costs of designing, production and assembly, as well as the waste of a considerable quantity of materials.

SUMMARY OF THE INVENTION

The main aim of the present invention is to provide a cannula for dispensing fluid products, particularly for vaginal and rectal applications, which is structurally and constructively very simple, that allows considerably curbing the production times and costs and limiting the wastes of materials.

A further object of the present invention is to provide a cannula for dispensing fluid products, particularly for vaginal and rectal applications, which is of limited overall dimensions, is easy to handle and which can be immediately used by users.

Another object of the present invention is to provide a cannula for dispensing fluid products, particularly for vaginal and rectal applications, which allows to overcome the mentioned drawbacks of the known art in the ambit of a simple, rational, easy, effective to use and low cost solution.

The above objects are achieved by the present cannula for dispensing fluid products, particularly for vaginal and rectal applications, characterized by the fact that it comprises at least a tubular body for containing at least a fluid product, having at least a first extremity at which at least a dispenser opening is obtained, and a second open extremity, opposed to the first extremity, at least a cover cap which can be fitted on said tubular body to close said dispenser opening, and at least a closing body which is associable with said tubular body to close said second extremity and which comprises at least a first element and at least a second element made in a single body piece and joined along tearable connection means, said second element being removable by tearing off said first element to act as a seal anti-tampering means and said first element being at least partially insertable through said second extremity and suitable for acting as a sliding piston inside said tubular body once said second element has been torn off.

More specifically, the first element of the closing body comprises a cylindrical member, and the second member has a round or annular shape. The round or annular second member serves as an anti-tampering seal, prior to the temporary retention members defined between said first and second members of the closing body being removed, or torn away, by the user of the cannula. By visually inspecting the cannula with the closing body partially inserted into an opening in the cannula, the user can determine if the cannula has been used previously or, perchance, has been subjected to tampering.

Additionally, in order to reduce the complexity of the molding and assembly steps necessary to produce a cannula in accordance with the principles of applicant's invention, the cover cap, upon removal from the tubular body of the cannula, is converted into a push rod for sliding the piston (or first part of the closing body) through the interior of the tubular body to efficiently discharge the product contained therein. The conversion is achieved by removing special, longitudal sections of the cover cap, along weakened or scored connections. The remaining sections of the cover cap are folded over to reduce the diameter of the cover cap. The cover cap, after such reduction, is inserted into an opening in the cannula to press against the piston, or first part of the closing body, and to slide same through the tubular body to discharge the fluid product contained therein.

BRIEF DESCRIPTION OF THE DRAWINGS

Other characteristics and advantages of the present invention will become more evident from the description of some preferred, but not sole, embodiments of a cannula for dispensing fluid products, particularly for vaginal and rectal applications, illustrated purely as an example but not limited to the annexed drawings in which:

FIG. 2 is an axonometric view of the closing body of the cannula of FIG. 1;

FIG. 3 is a section view along the plane III-III of FIG. 1;

FIG. 4 is an axonometric view of the tubular body of the cannula of FIG. 1;

FIG. 5 is an axonometric view of the cover cap of the cannula of FIG. 1;

FIG. 6 is a section view of the cannula of FIG. 1 in packaging configuration;

FIGS. 7-9 show, in a sequence of axonometric views, the use method of the cannula of FIG. 1;

FIG. 10 is a section view of a second embodiment of the cannula according to the invention in packaging configuration.

DETAILED DESCRIPTION OF THE EMBODIMENTS

Figure 1:
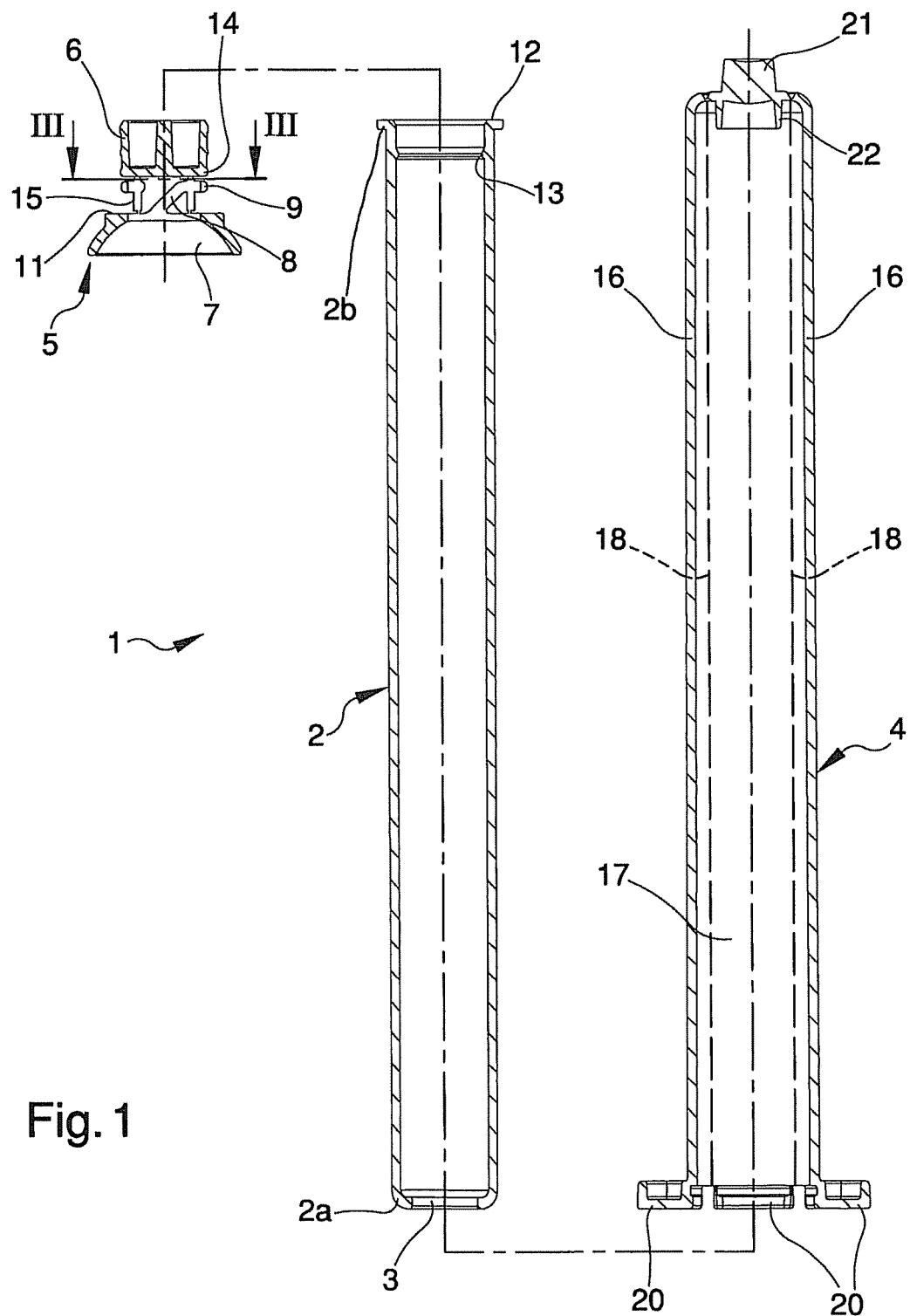
FIG. 1 is an exploded and section view of a first embodiment of the cannula according to the invention.

With particular reference to the embodiment of the figures from 1 to 9, globally by 1 has been indicated a cannula for dispensing fluid products, particularly for vaginal and rectal applications.

In this respect, it is specified that in this application by the term fluid products includes not only liquid products but also viscous products, e.g., in the state of paste and gel, and powdered products, in particular very fine powders distinguished by great flowability.

The cannula 1 comprises a tubular body 2 which is meant to contain the fluid product P.

The tubular body 2 is shaped like a straight cylinder and has a first extremity 2a at which is obtained at least a dispenser opening 3.

In the embodiment of the figures from 1 to 9 there is only one dispenser opening 3 which is obtained axially, meaning it extends crossways to the longitudinal direction of the tubular body 2.

Alternative embodiments of the invention are however possible in which several dispenser openings 3 are provided and/or in which these are obtained on the side surface of the first extremity 2a.

On the opposite side with respect to the first extremity 2a, the tubular body 2 has a second open extremity 2b.

The cannula 1 also comprises a cover cap 4 which is made separate from the tubular body 2, and which is fitted onto the body to close the dispenser opening 3.

To close the second extremity 2b, on the other hand, the cannula 1 comprises a closing body 5, this component also being formed separate from the tubular body 2.

The closing body 5 comprises a first element 6 and a second element 7 made in a single body piece and joined along tearable connection means 8, 9, 10.

In detail, the second element 7 has a substantially round or annular shape and can be torn off the first element 6 to act as an anti-tampering seal, indisputably indicating when the cannula 1 has actually been opened by a user.

The first element 6, on the other hand, has a substantially hollow cylindrical shape and can be inserted snugly through the second extremity 2b to act as a piston sliding inside the tubular body 2 once the second element, or seal, 7 has been torn off.

For this purpose, the cannula 1 has temporary retention means 11, 12, 13, 14 suitable for retaining the closing body 5 in a packaging configuration in which the first element 6 is inserted in the tubular body 2 near to the second extremity 2b.

The temporary retention means 11, 12, 13, 14, comprise a shoulder edge 11, which is obtained or formed on the second element 7, and a corresponding locator edge 12, which is obtained or formed around the second extremity 2b of the tubular body 2. The shoulder edge 11 contacts locator edge 12 which acts as a stop and prevents further insertion of the closing body 5 into the tubular body 2.

The temporary retention means 11, 12, 13, 14 also comprise a stop tooth 13, which is obtained in centripetal overhang on the inner surface of the tubular body 2, and a corresponding locator surface 14, which is obtained on the first element 6 and which can be engaged against the stop tooth 13 to prevent the withdrawal of the first element 6 from the tubular body 2.

The tearable connection means 8, 9, 10 comprise a removal arm 8, 9 stably joined to the second element 7 and connected to the first element 6 by interposition of a plurality of weakened-section connection points 10.

The removal arm 8, 9, comprises a first portion 8, which extends substantially obliquely from the second element 7, and a second portion 9, with substantially annular conformation, which develops along a lying plane substantially at right angles to the longitudinal direction of the tubular body 2, and along which are distributed the connection points 10, shown in FIGS. 2 and 3.

Between the second portion 9 and the second element 7, stiffening bridges 15 are also provided which permit transmitting thrust forces from the second element 7 towards the first element 6.

The cover cap 4 is made in a single body piece that converts into a push rod 25 insertable in the tubular body 2 to press the first element 6 sliding along the tubular body 2 and allow dispensing the fluid product P through the dispenser opening 3.

For this purpose, the cover cap 4 is split into a plurality of first longitudinal sections 16 and into at least a second longitudinal section 17 which can be torn off the first longitudinal sections 16.

The second longitudinal section 17, in particular, is joined to the first longitudinal sections 16 along weakened-section longitudinal connection lines 18 that extend substantially for the entire length of the cannula 1.

The first longitudinal sections 16, on the other hand, can be folded along longitudinal folding lines 19 that extend substantially along the entire length of the cannula 1.

Once the second longitudinal section 17 has been torn off, in practice, the first longitudinal sections 16 are folded on themselves, to define the push rod 25.

The transversal dimensions of the first longitudinal sections 16 folded on themselves are in fact considerably less than the diameter of the cover cap 4 and allow the insertion inside the tubular body 2 to push the first element 6.

In the embodiment shown in the figures from 1 to 9, therefore, the push rod 25 coincides with at least a part of the cover cap 4.

To make gripping by the user easier, the first longitudinal sections 16 and the second longitudinal section 17 have gripping fins 20 obtained at the extremity of the cover cap 4 corresponding to the second extremity 2b of the tubular body 2.

In particular, the gripping fins 20 of the first longitudinal sections 16 are distributed in an asymmetric way, as is clearly visible in the FIG. 5.

At the opposite extremity, the cover cap 4 has a bottom wall 21 which is substantially transversal to the longitudinal direction of the tubular body 2 and which can be fitted in front of the first extremity 2a.

At the bottom wall 21, the cover cap 4 comprises an inner shutter body 22 which can be inserted snugly in the dispenser opening 3.

Both the bottom wall 21 and the shutter body 22 are part of the second longitudinal section 17 and with this can be torn off the first longitudinal sections 16.

The operation of the cannula 1 shown in the figures from 1 to 9 is the following.

The cannula 1 is made in just three separate pieces, or components, tubular body 2, cover cap 4 and closing body 5, assembled together.

To make up the cannula 1 the cover cap 4 is fitted on the tubular body 2, the tubular body 2 is pre-filled with the fluid product P, and then the second extremity 2b is closed with the closing body 5.

The insertion of the closing body 5 in the tubular body 2 is done by pushing the second element 7 until the shoulder edge 11 is up against the locator edge 12 and the first element 6 is blocked on the stop tooth 13; in this phase, the thrust force is transmitted from the second element 7 to the first element 6 through the stiffening bridges 15.

The cannula 1 is then distributed on the market in the packaging configuration shown in the FIG. 6, with the tubular body 2 pre-filled, covered by the cover cap 4 and sealed by the closing body 5.

At the time of use, the user removes the second element 7 and the cover cap 4 from the tubular body 2 (FIG. 7).

For this purpose, it is underlined that the removal of the second element 7 takes place simply by moving the second element 7 away from the second extremity 2b.

Such movement also drags outwards the removal arm 8, 9 which, by means of the first portion 8, is firmly joined to the second element 7.

The particular conformation of the removal arm 8, 9 thus allows tearing the connection points 10 in a sequential way; in other words, the annular shape of the second portion 9 causes the connection points 10 to be placed under tension and torn one after the other and not all at the same time.

This way, the force transmitted to the first element 6 is very limited and is easily discharged or dissipated onto the stop tooth 13.

The removal of the cover cap 4, on the other hand, occurs by tearing the longitudinal connection lines 18.

For this purpose, all the user has to do is tear the second longitudinal section 17 by levering the corresponding gripping fin 20.

The second longitudinal section 17, in practice, also acts as an anti-tampering seal for it indisputably shows whether the cannula 1 has been opened.

The first longitudinal sections 16, on the other hand, are folded on themselves along the longitudinal folding lines 19 (FIG. 8) and are used as push rod 25 to push the first element 6 in a sliding manner along the tubular body 2 (FIG. 9).

For this purpose, it is underlined that in this phase the particular asymmetric distribution of the gripping fins 20 easily permits folding the first longitudinal sections 16 superimposing at least in part the torn flaps, so as to facilitate the forming of the push rod 25 and its subsequent insertion into the tubular body 2.

In an alternative embodiment of the invention shown in the FIG. 10, the cannula 1 consists of a tubular body 2, a closing body 5 and a cover cap 4 substantially identical to those of the figures from 1 to 9. However, in the alternative embodiment the push rod 25 does not coincide with the cover cap 4, but is composed of an elongated slat 23 joined to the cover cap 4 by the interposition of a pair of tearable connection segments 24.

In the embodiment of FIG. 10 as well therefore, the cannula 1 is made in just three separated pieces in which, however, it is not the first longitudinal sections 16 of the cover cap 4 that act as a push rod 25, but the elongated slat 23.

The operation of this embodiment is substantially the same as that previously described and illustrated, with the difference that before use, the elongated slat 23 must be separated from the cover cap 4, by tearing the connection segments 24, in order to use it as a push rod 25 to press the first element 6 along the interior of tubular body 2.

It has in practice been found how the invention described achieves the intended objects.

In this respect, it is underlined that the present cannula for the dispensing of fluid products, particularly for vaginal and rectal applications, can be fabricated by assembly of just three components, permitting a considerable reduction in production times and costs, as well as of material wastes.

It is further pointed out that, thanks to a simple and compact structure, the cannula according to the present invention has small overall dimensions, is particularly simple and handy to use, minimizes that amount of wasted material, yet is easy to mold with a minimum number of components, and is easy and simple to assemble. Consequently, the appended claims should be construed in a manner consistent with the scope of applicant's invention, and should not be limited to their literal terms.

The invention claimed is:

1. A cannula for dispensing products, particularly for vaginal and rectal applications, said cannula comprising:
   a) a tubular body for containing fluid product,
   b) said tubular body having a first extremity with a dispenser opening, and a second extremity with a second opening,
   c) a closing body operatively associated with said tubular body to close said second opening,
   d) said closing body including a first element extending at least partially through said second opening, said first element comprising a piston,
   e) a cover cap circumferentially surrounding said tubular body along its entire length and closing said dispenser opening,
   f) a plurality of weakened-section longitudinal connection lines dividing said cover cap into a plurality of sections,
   g) removing at least one of said longitudinal sections of said cover cap and folding the remaining longitudinal sections over said weakened-section longitudinal connection lines to reduce the diameter of the cover cap and convert the cover cap into a push rod, and
   h) said push rod engaging said piston to slide same through said tubular body to discharge fluid product through said dispenser opening.

2. The cannula according to claim 1 wherein said sections include gripping fins located at one end of said longitudinal sections to facilitate tearing the sections away from the cover cap.

3. The cannula according to claim 1 wherein said closing body further includes a second element, said second element being annular in shape and projecting from said tubular body to serve as an anti-tamper seal.

4. The cannula according to claim 3 wherein tearable connections join said first element and said second element together, said second element being torn away from said tearable first element along said connections prior to using the cannula.

* * * * *